(12) United States Patent
Rapaport et al.

(10) Patent No.: US 7,093,527 B2
(45) Date of Patent: Aug. 22, 2006

(54) METHOD AND APPARATUS FOR MAKING INTRALUMINAL IMPLANTS AND CONSTRUCTION PARTICULARLY USEFUL IN SUCH METHOD AND APPARATUS

(75) Inventors: Avraham Rapaport, Tel Aviv (IL); Boaz Nishri, Maagan Michael (IL); Gilad Cibulski, Moshav Herut (IL)

(73) Assignee: Surpass Medical Ltd., Tel-Aviv (IL)

( * ) Notice: Subject to any disclaimer, the term of this patent is extended or adjusted under 35 U.S.C. 154(b) by 0 days.

(21) Appl. No.: 10/862,397

(22) Filed: Jun. 8, 2004

(65) Prior Publication Data

US 2004/0254633 A1 Dec. 16, 2004

Related U.S. Application Data

(60) Provisional application No. 60/477,030, filed on Jun. 10, 2003.

(51) Int. Cl.
*D04C 3/40* (2006.01)
(52) U.S. Cl. .......................................... 87/34
(58) Field of Classification Search .............. 87/9, 87/11, 34
See application file for complete search history.

(56) References Cited

U.S. PATENT DOCUMENTS

| | | | |
|---|---|---|---|
| 1,064,407 A | 6/1913 | Wardwell | |
| 1,423,587 A | 7/1922 | Wardwell | |
| 2,557,816 A * | 6/1951 | Di Palma | ............ 87/34 |
| 3,287,194 A * | 11/1966 | Waddell, Jr. | ............ 156/144 |
| 3,783,786 A | 1/1974 | Ellison | |
| 4,616,553 A | 10/1986 | Nixon | |
| 4,655,771 A | 4/1987 | Wallsten | |
| 4,846,908 A * | 7/1989 | Aldrich et al. | ............ 156/148 |
| 4,893,543 A * | 1/1990 | Phillips | ............ 87/34 |
| 4,954,126 A | 9/1990 | Wallsten | |
| 5,016,516 A * | 5/1991 | Aldrich et al. | ............ 87/8 |
| 5,061,275 A | 10/1991 | Wallsten | |
| 5,203,249 A * | 4/1993 | Adams et al. | ............ 87/34 |
| 5,922,019 A | 7/1999 | Hankh et al. | |
| 5,931,077 A | 8/1999 | DeYoung | |
| 5,974,938 A | 11/1999 | Lloyd | |
| 6,250,193 B1 * | 6/2001 | Head | ............ 87/2 |
| 6,283,992 B1 | 9/2001 | Hankh et al. | |
| 6,533,810 B1 | 3/2003 | Hankh et al. | |
| 2002/0160068 A1 * | 10/2002 | Nakamura | ............ 425/112 |

* cited by examiner

Primary Examiner—Shaun R Hurley

(57) ABSTRACT

A method of and an apparatus for making a braided intraluminal implant, by providing a mandrel having at least one small-diameter section joined at least at one end to a large-diameter section; interweaving a plurality of filaments to form a tubular braid enclosing at least a part of the small-diameter section and at least a part of the large-diameter section; and cutting the tubular braid to produce a tubular braid segment having outwardly flared ends at its opposite ends. One flared end is produced by the large-diameter section of the mandrel, and the opposite outwardly flared end may be produced either by another large-diameter section of the mandrel, or by cutting the tubular braid at a portion formed by the small-diameter section of the mandrel but at a location wherein the release of stresses in the filaments inherently produces an outward flaring of the braid at that end.

15 Claims, 10 Drawing Sheets

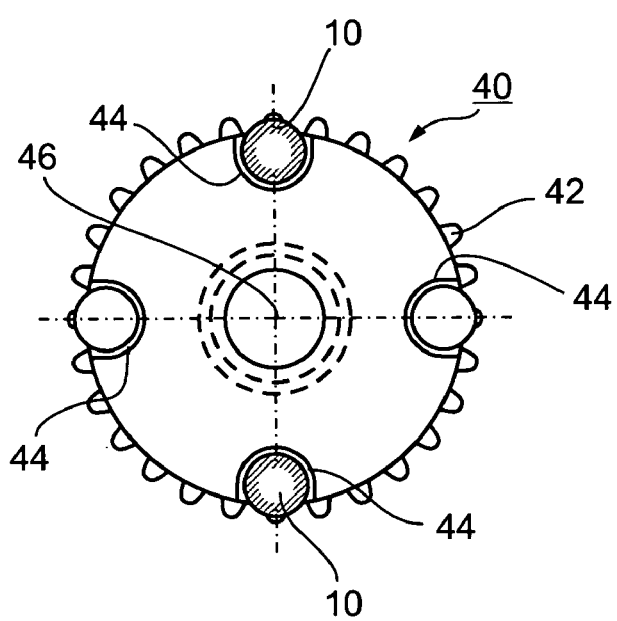
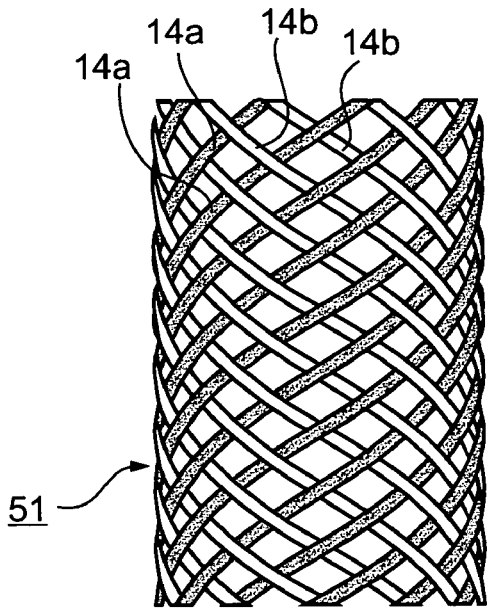
Fig. 4    Fig. 6
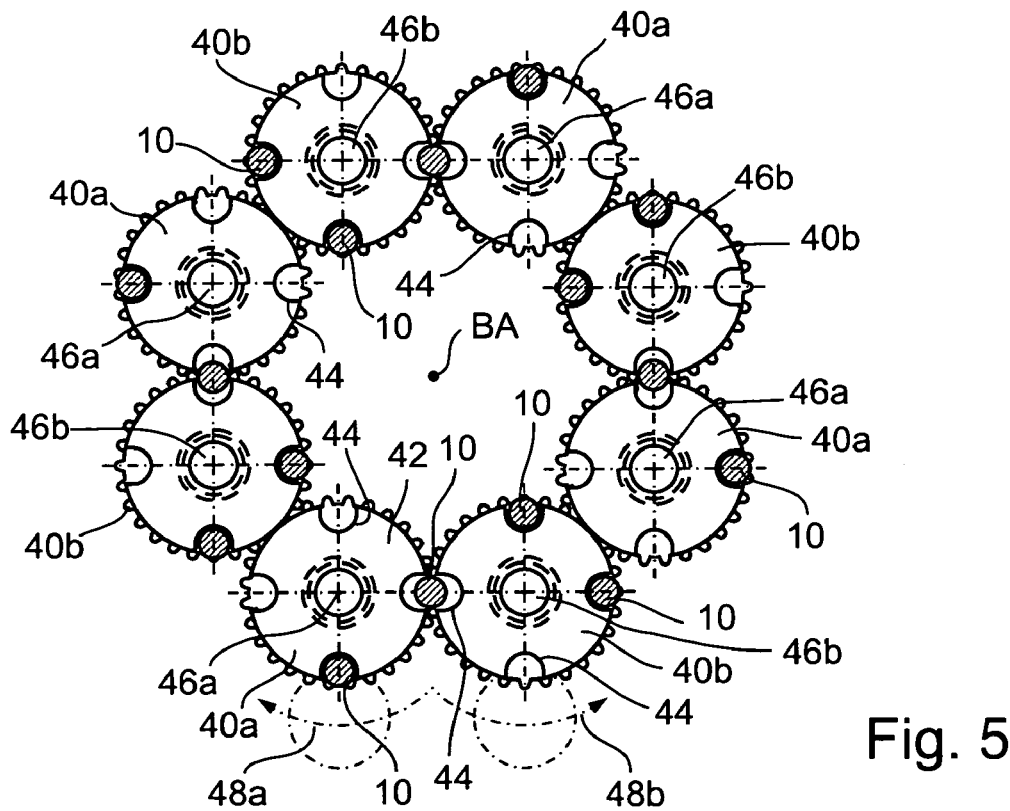
Fig. 5

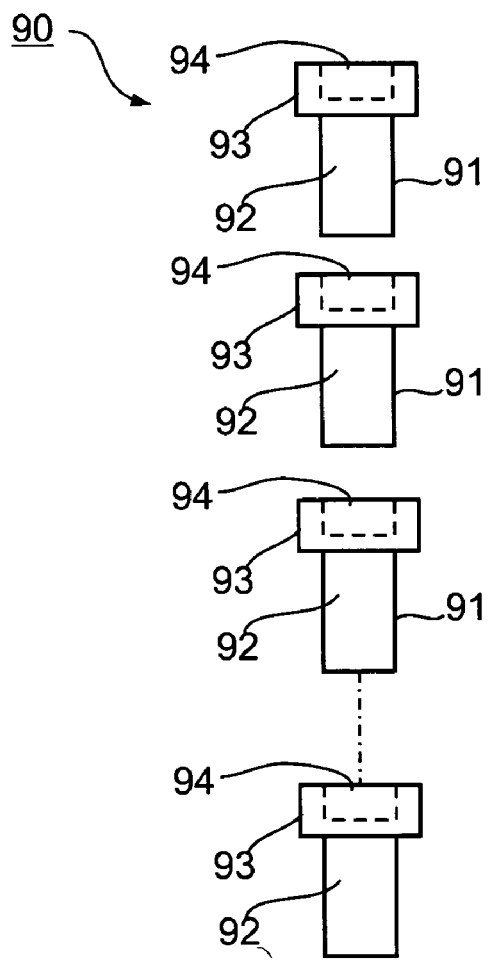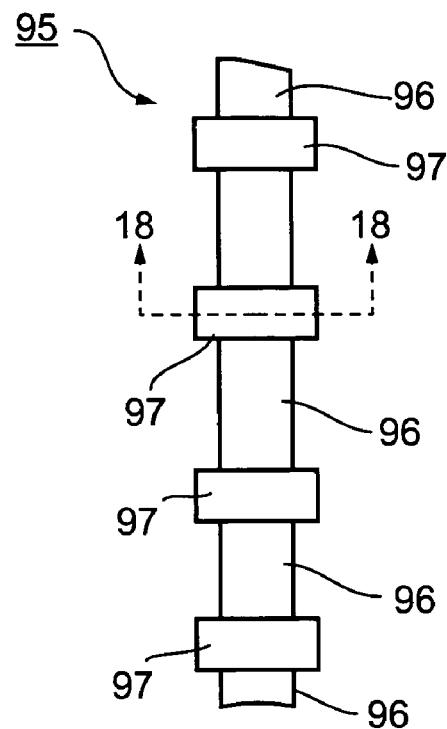
Fig. 16
Fig. 17
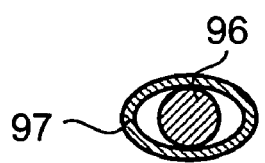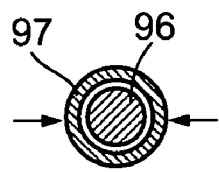
Fig. 18a      Fig. 18b

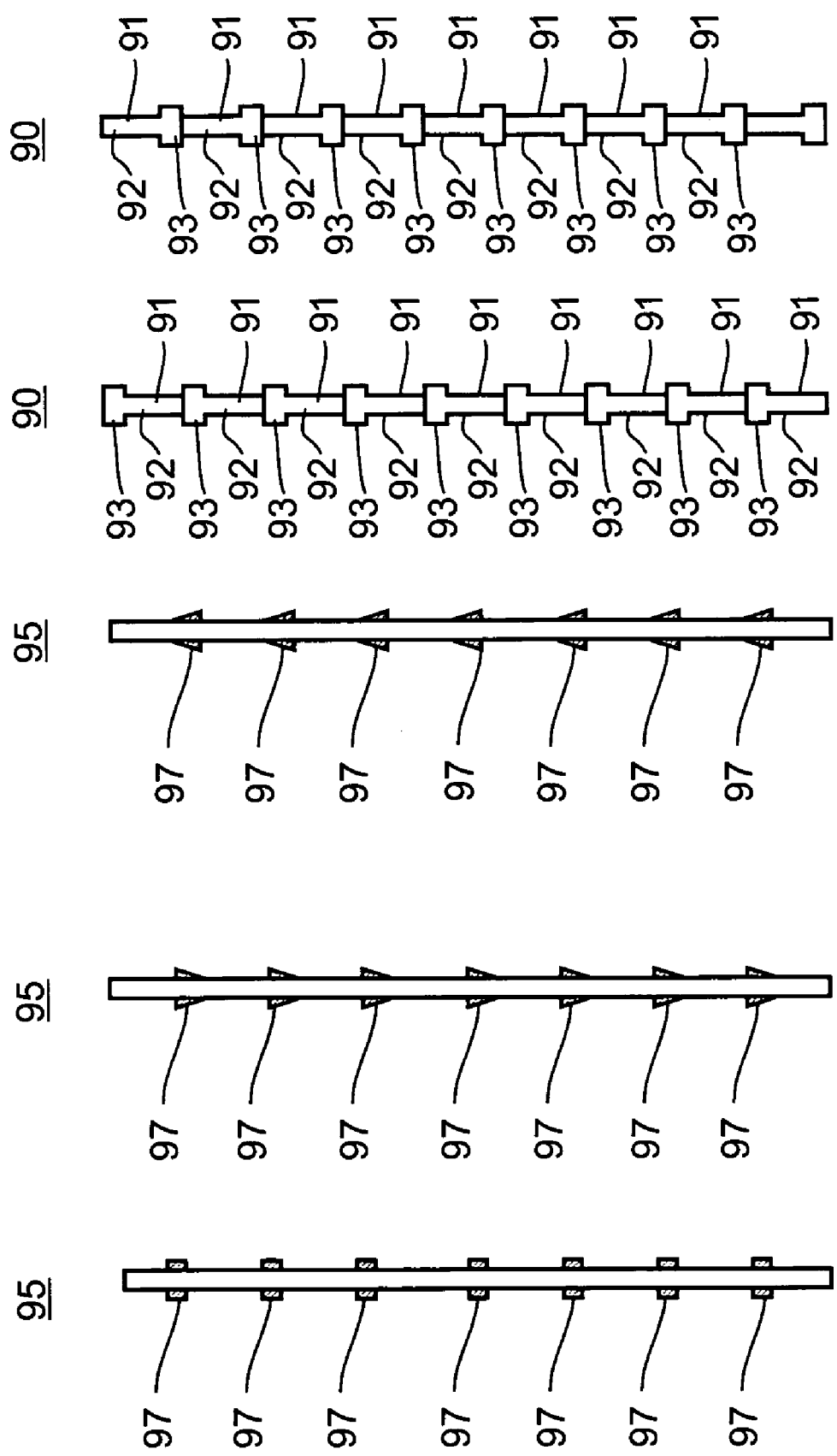

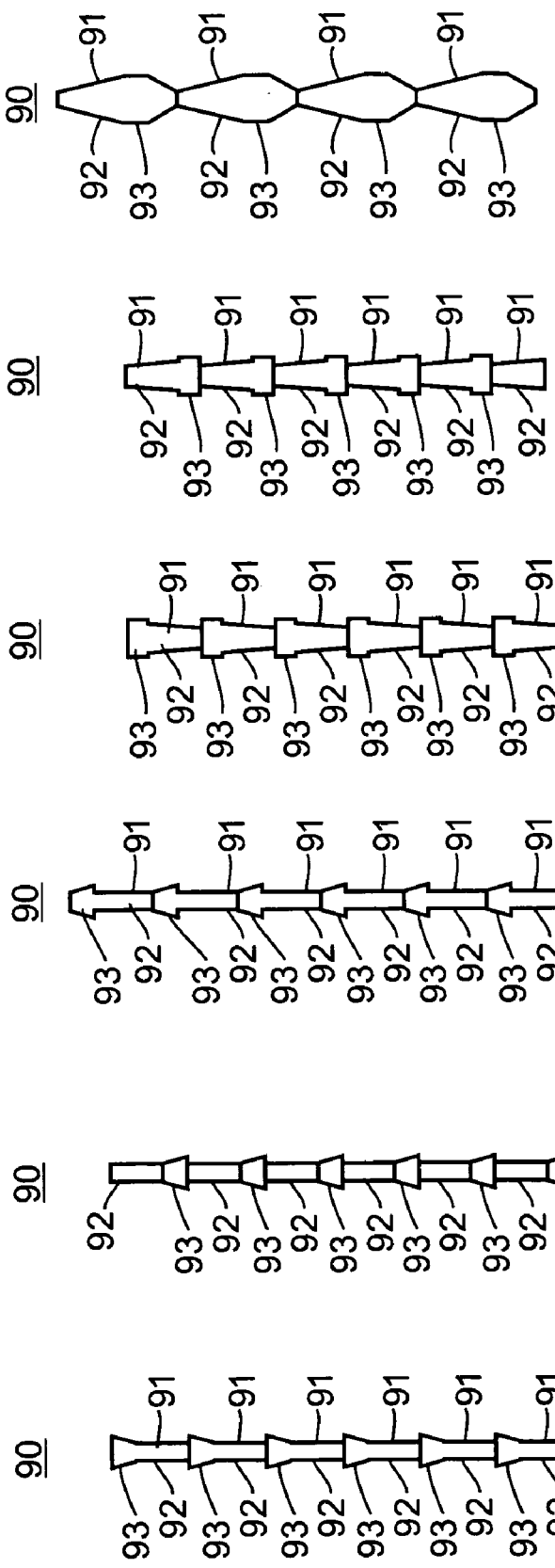

METHOD AND APPARATUS FOR MAKING INTRALUMINAL IMPLANTS AND CONSTRUCTION PARTICULARLY USEFUL IN SUCH METHOD AND APPARATUS

CROSS-REFERENCE TO RELATED APPLICATION

This application claims priority from U.S. Provisional Patent Application No. 60/477,030 filed Jun. 10, 2003 the contents of which are incorporated herein by reference.

FIELD AND BACKGROUND OF THE INVENTION

The present invention relates to a method and apparatus for making braided intraluminal implants, and also to a mandrel construction particularly useful in such method and apparatus.

Intraluminal devices, such as stents, filters and diverters are increasingly being used as implants within an artery, vein, or other tubular body vessel for effecting various medical treatments of the body. One type of intraluminal implant used for this purpose is the braided type produced by braiding machines which interweave a plurality of filaments around a mandrel aligned with the braiding axis. At the time of implantation, the braided tube is of reduced diameter (e.g., by enclosing it within an outer constricting tube) to enable the braided tube to be fed (e.g., by a catheter) via the lumen to the implantation site. Upon reaching the implantation site the braided tube is expanded (e.g., by removing the outer constricting tube), thereby firmly fixing the braided tube within the vessel wall.

It has been found that the contact of the braided tube implant with the vessel wall is enhanced if the outer ends of the braided tube are outwardly flared. This has proved difficult to accomplish using conventional braiding machines and conventional mandrels.

OBJECTS AND BRIEF SUMMARY OF THE PRESENT INVENTION

An object of the present invention is to provide a method, and also apparatus, for making a braided tube intraluminal implant having outwardly flared ends in a manner which enables the use of conventional braiding machines. Another object of the invention is provide a mandrel construction particularly useful in such a method and apparatus.

According to one aspect of the present invention, there is provided a method of making a braided intraluminal implant, comprising: providing a mandrel having at least one small-diameter section joined at least at one end to a large-diameter section; interweaving a plurality of filaments devoid of a binder material to form a tubular braid enclosing at least a part of the small-diameter section and at least a part of the large-diameter section; and, while the filaments remain devoid of a binder material such that the filaments are supported solely in the tubular braid by the mandrel, cutting the tubular braid to produce a tubular braid segment having outwardly flared ends at its opposite ends.

Several embodiments of the invention are described below for producing the outwardly flared ends of each of the tubular braided segments.

According to one described embodiment, the continuous tubular braid is cut along an enlarged portion thereof formed by a large-diameter section of the mandrel to produce each of the outwardly flared ends of the tubular braid segment.

According to a second described preferred embodiment, the tubular braid is cut along a first cut line on an enlarged portion thereof formed by the large-diameter section of the mandrel to produce an outward flaring at the first cut line defining one end of the tubular braid segment; the tubular braid being cut along a second cut line on a portion thereof formed by the small-diameter segment of the mandrel at a location of the tubular braid where the release of stresses in the filaments of the tubular braid inherently produces an outward flaring of the braid at the second cut line defining the opposite end of the tubular braid segment.

According to another aspect of the present invention, there is provided a mandrel for use with a braiding machine for making braided intraluminal implants; the mandrel comprising at least one small-diameter section joined at least at one end to a large-diameter-section; the mandrel being dimensioned to enable a plurality of filaments to be interwoven thereon to produce braided intraluminal implants of a diameter corresponding to the small-diameter section and having at fast one flared end formed by the large-diameter section; the mandrel being of a length many times that of the braided intraluminal implants to be made, such that a continuous length of a tubular braid may be formed on the mandrel and then cut into a plurality of the tubular braid segments; the mandrel being constructed of a plurality of modular units, each having a cylindrical, conical or tapered section integrally formed at one end with an enlarged head, having an axially-extending bore of a diameter to receive the end of the cylindrical, conical or tapered section of another modular unit.

In one preferred embodiment of the invention described below, the mandrel is constructed of a plurality of modular units, each including a cylindrical, conical, or tapered section formed at one end with an enlarged cylindrical, conical or tapered head. Each of the enlarged heads is formed with an axially-extending bore (or similar formation) of a diameter to receive the end of the cylindrical, conical or tapered section of another modular unit. After a tubular braid is cut from the continuous length, a modular unit is removed to permit the cut tubular braid segment to be conveniently removed.

In a second described preferred embodiment, the mandrel is constructed of a cylindrical, conical or tapered rod having a plurality of rings removably received at spaced locations along the length of the rod to define the large-diameter sections of the mandrel. Each of the rings is an elastic ring of a non-circular configuration in its free state so as to be elastically retained on the rod and conveniently removable therefrom by manually distorting the ring towards a circular configuration. After a tubular braid segment is cut from the continuous length, a ring is removed from the rod to permit the cut tubular braid to be conveniently removed.

According to a still further aspect of the present invention, there is provided apparatus for making braided intraluminal implants, comprising: a mandrel as defined herein; and a braiding machine for interweaving a plurality of filaments around the mandrel.

As will be described more particularly below, the foregoing method, apparatus, and mandrel construction permit the efficient production, of braided tubes having flared ends particularly useful as intraluminal implants.

Further features and advantages of the invention will be apparent from the description below.

BRIEF DESCRIPTION OF THE DRAWINGS

The invention is herein described, by way of example only, with reference to the accompanying drawings, wherein:

FIGS. 4 and 5 illustrate one loading arrangement for loading the braiding apparatus of FIG. 1 to produce a particular braid pattern, commonly called a Herringbone Pattern, in which each filament of one group of spools is interweaved under and over two filaments of the other group of spools;

FIG. 6 illustrates the Herringbone Pattern produced by the arrangement of FIGS. 4 and 5;

FIG. 16 illustrates one particular construction of the mandrel of FIG. 13;

FIG. 17 illustrates another particular construction of the mandrel of FIG. 13;

FIG. 18a is a sectional view along line 18—18 of FIG. 17, illustrating a removable ring thereon in its normal operative condition during the formation of the braided tubing thereover;

FIG. 18b is a view similar to that of FIG. 18a, but illustrating the released condition of the ring, produced by manually squeezing it towards a circular configuration, to permit the ring to be conveniently assembled to and removed from the mandrel; and FIGS. 19a–19k illustrate examples of other configurations of mandrels that may be used.

It is to be understood that the foregoing drawings, and the description below, are provided primarily for purposes of facilitating understanding the conceptual aspects of the invention and various possible embodiments thereof, including what is presently considered to be preferred embodiments. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

Braiding Machine Construction (FIGS. 1–12)

The invention is particularly useful when embodied in the "Maypole" type of braiding machine, as sold by Steeger USA, Inc. of Spartanburg, South Carolina, or by the New England Butt Division of Wardwell Braiding Machine Company. The invention is therefore described below with respect to such a braiding machine. The invention is particularly useful, and is therefore also described below, for making braided tubes of ultra-fine filaments, in the order of 50 μm, for use in medical intraluminal implants, such as stents, filters and diverters, for implantation in the human body. It will be appreciated, as indicated above, that the invention could also be advantageously implemented in other braiding machines and methods, and could be used for making braids for other applications and for other sized filaments.

Figure 1:
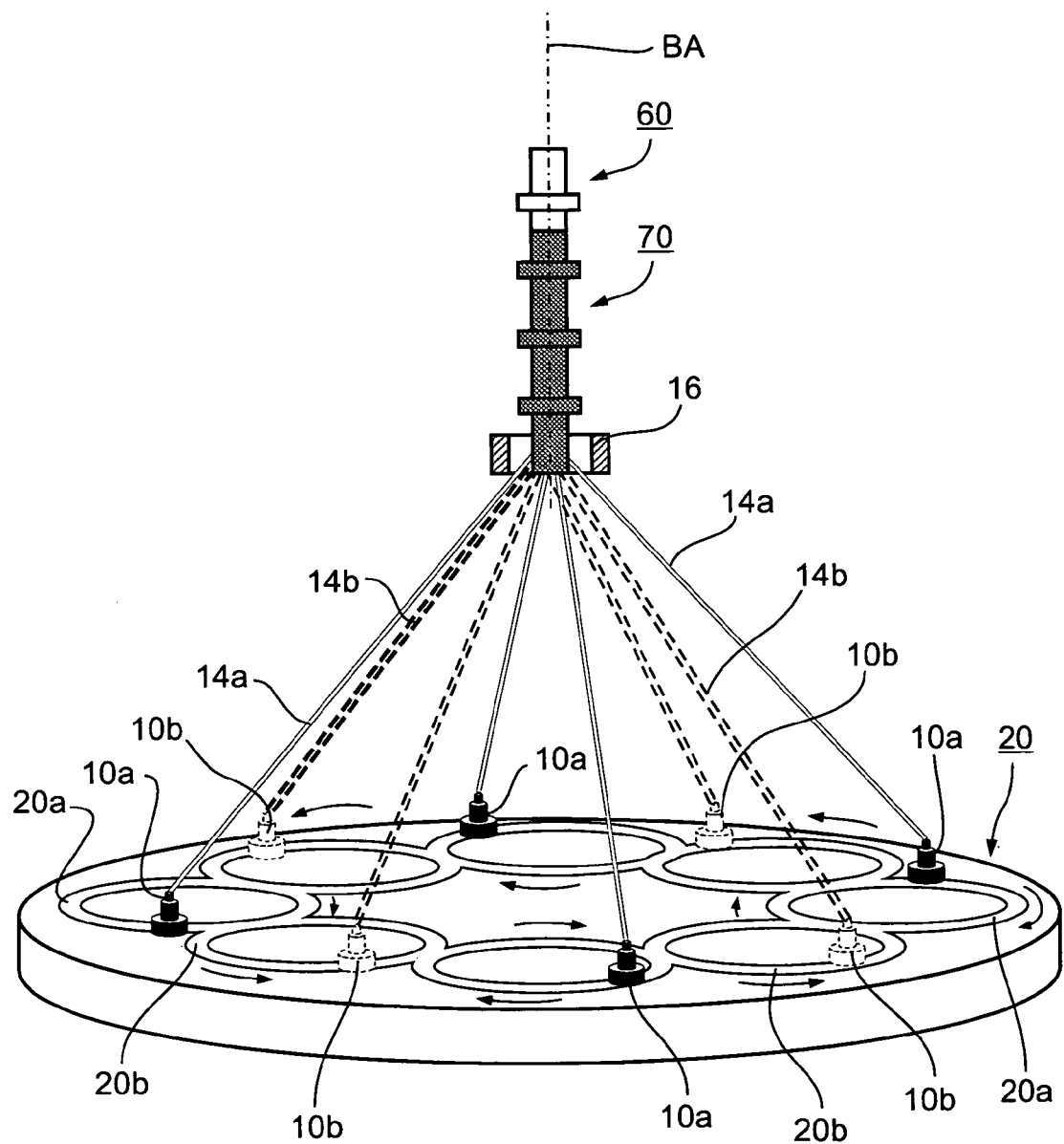
FIG. 1 diagrammatically illustrates one form of braiding apparatus that may be used for making intraluminal implants in accordance with the present invention.

FIG. 1 diagrammatically illustrates a braiding machine of the foregoing Maypole type. It includes a plurality of carriers divided into two groups, 10a, 10b. Each carrier mounts a spool 12 (FIG. 2) carrying supply of a filament 14 to be interwoven into a braid. The filaments 14 of all the carriers 10a, 10b are converged towards the braiding axis BA through a braiding guide 16 located distally from the plurality of carriers 10a, 10b. The filaments 14 are thus interwoven into a braid 70 about a mandrel 60 passing through the braiding guide 16. In FIG. 1, the mandrel is generally designated 60 and is more particularly illustrated in FIG. 13, whereas the braided tube formed thereon is generally designated 70 and is more particularly illustrated in FIGS. 14a–14c below.

The illustrated apparatus further includes an interweaving mechanism housed within a housing generally designated 20 for driving the carriers 10a, 10b and for paying out the filaments 14 from their respective spools 12. The filaments are thus payed out in an interweaving manner towards the braiding guide 16 to form the braid 70 about the mandrel 60.

The braiding apparatus illustrated in FIG. 1 is of the vertical type; that is, the braiding axis BA of the mandrel 60, about which the braid 70 is formed, extends in the vertical direction. A vertical-type braiding apparatus provides more convenient access by the operator to various parts of the apparatus than the horizontal-type apparatus wherein the braid is formed about a horizontal axis. In the illustrated vertical-type apparatus, the interweaving mechanism is within a flat horizontal housing 20, and includes a drive for driving the two groups of carriers 10a, 10b such as to interweave the filaments 14 of their respective spools as they are payed out towards the braiding guide 16. Each carrier of the two groups 10a, 10b illustrated in FIG. 1 carries a spool of the filament 14 to be payed out by the respective carrier. Carriers 10a are arrayed in a circular array around the braiding axis BA and are driven in one direction about that axis. Carriers 10b are also arrayed, in a circular array around the braiding axis BA, alternatingly with respect to carriers 10a, and are driven in the opposite direction about that axis.

For purposes of example, FIG. 1 illustrates the filaments 14a payed out from carriers 10a in full lines, with carriers 10a being driven about braiding axis BA in the clockwise direction; whereas the filaments 14b payed out from carriers 10b, shown in broken lines, with carriers 10b being driven about braiding axis BA in the counter-clockwise direction. The flat horizontal housing 20 houses a drive mechanism (to be more particularly described below with respect to FIGS. 4–12) which drives carriers 10a along a circuitous path shown as shaded path 20a, and drives the carriers 10b along another circuitous path, shown by unshaded path 20b, intersecting with the shaded circuitous path 20a. As shown in FIG. 1, the circuitous path 20a for carriers 10a, and also the circuitous path 20b for carriers 10b, bring the respective carriers 10a, 10b radially inwardly and outwardly with respect to the braiding axis BA, as the carriers move around the braiding axis.

Since such an interweaving mechanism is well known in braiding machines of this type, as described for example in the published literature available from the manufacturers of such machines, full details of the construction and operation of such an interweaving mechanism are not set forth herein.

Figure 2:
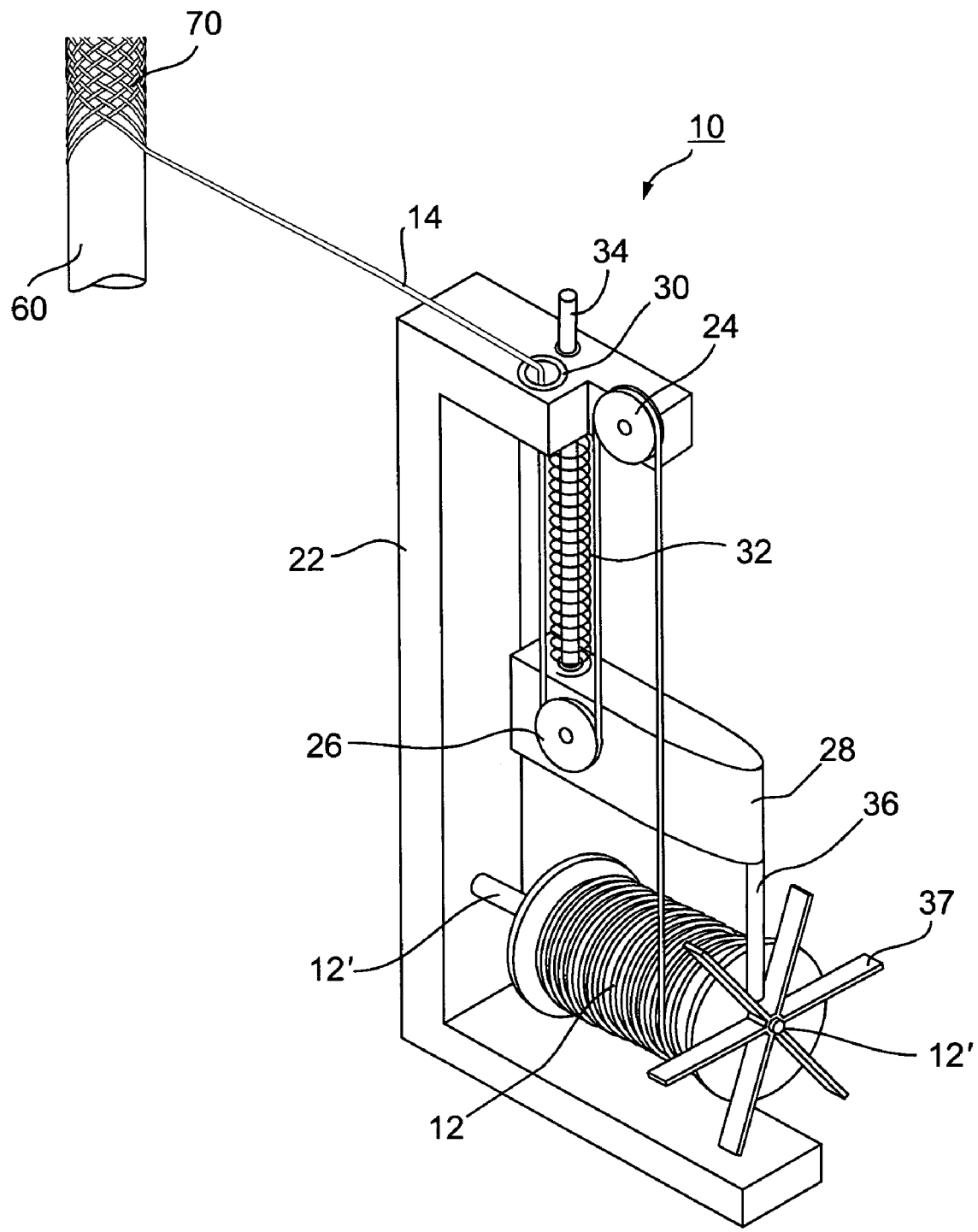
FIG. 2 illustrates one of the driven carriers for one of the filament spools in a commercially available braiding machine which may be used in the apparatus of FIG. 1, and particularly indicating the span of the filament from its spool towards the braiding point on the mandrel where all the filaments are converged into a braid.

FIG. 2 illustrates one structure that may be provided for each of the carriers 10a, 10b, mounting one of the spools 12 for the respective filament 14. As shown in FIG. 2, each carrier, therein generally designated 10, includes a vertically-extending mounting member 22 rotatably mounting the respective filament spool 12 for rotation about a horizontal axis. Spool 12 could be mounted to rotate with respect to its shaft 12' or could be fixed to its shaft and both rotated with respect to mounting member 22.

In the embodiment illustrated in FIG. 2, each carrier mounting member 22 mounts an upper roller 24 and a lower roller 26 above the spool 12, each roller being rotatably mounted about an axis parallel to the spool axis. The upper roller 24 is rotatably mounted on the carrier mounting member 22; whereas the lower roller 26 is rotatably mounted on a movable mounting member 28 which is vertically displaceable with respect to roller 24 and mounting member 22. Each filament 14 is fed from its respective spool 12 over the upper roller 24, and under the lower, vertically-displaceable roller 26, and through an upper eyelet 30 to braiding guide 16 of FIG. 1. Braiding guide 16 converges all the filaments 14 to produce the braid 70 over the mandrel 60 coaxial with the braiding axis BA.

As indicated earlier, one of the problems in braiding machines of this type is the need for applying the appropriate tension to the filaments 14 so as not to break or deform the filament by an unduly large tension, or to produce a sag in the filament, particularly the portion between the upper eyelet 30 and the braiding guide 16, which may cause entanglement with other filaments as their respective carriers 10 are rotated about the braiding axis BA. Braiding machines of this type usually include a spring arrangement for applying the appropriate tension to the filaments. FIG. 2 illustrates such a spring, at 32, applied between the carrier mounting member 22 mounting the upper roller 24, and the vertically-displaceable mounting member 28 mounting the lower roller 26. The vertical displacement of mounting member 28, and thereby of the lower roller 26, is guided by a rod 34 movable within an opening in the upper roller mounting member 22.

FIG. 2 further includes the vertically-displaceable mounting member 28 for the lower roller 26 as provided with a depending finger 36 movable within recesses defined by a retainer member 37 fixed to the spool shaft 12' to restrain the spool shaft from free rotation.

Since the force applied by springs, such as spring 32, generally varies with the loaded condition of the spring, the tensioning force produced by such a spring would generally not be constant and uniform because of the movement of the carriers, radially inwardly and outwardly, as they are driven in opposite direction about the braiding axis BA. This problem is particularly acute when braiding ultra-fine filaments, such as wires of 50 μm in diameter and less, since an unduly high tensioning force applied at any time to such a filament to avoid sagging and the danger of filament entanglement, is liable to rupture or deform the filament before it is formed into the braid.

Figure 3:
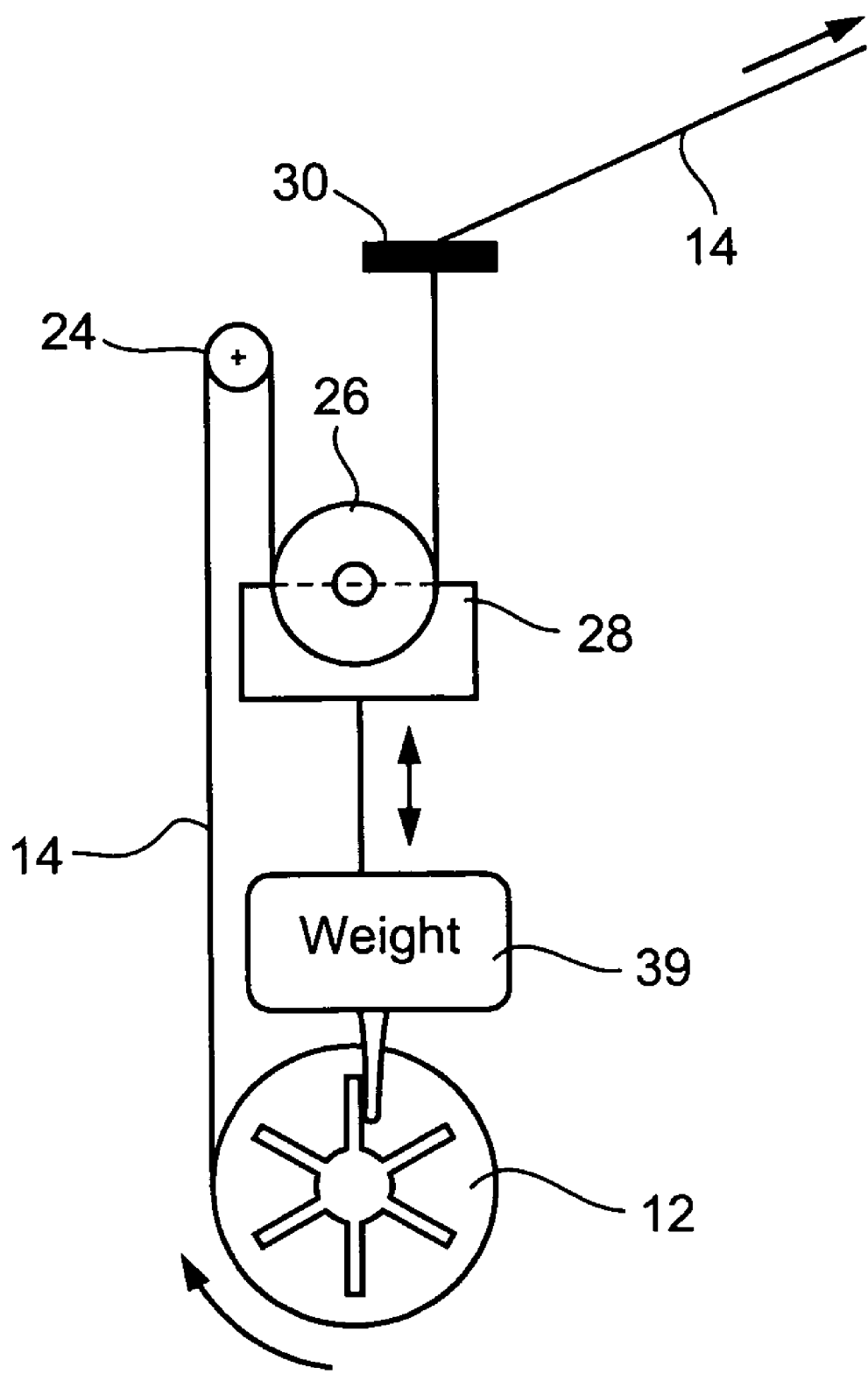
FIG. 3 illustrates a preferred manner of tensioning each of the filaments from its respective spool toward the braiding point in order to produce a uniform tension such as to reduce the possibility of filament rupture or deformation as well as filament entanglement.

FIG. 3 diagrammatically illustrates how the filaments 14 are preferably tensioned in a constant and uniform manner in order to minimize the possibility of over-tensioning likely to cause breakage or deformation, or under-tensioning likely to cause entanglement. Thus, as shown in FIG. 3, the vertically displaceable roller 26 in each of the carriers 10 is provided with a weight, shown at 39, which applies a gravitational tensioning force to the filament 14 passing under the lower roller 26 mounted on mounting member 28. Since this tensioning force is a gravitational force applied by the weight 39, it is constant and uniform, and does not vary with the circuitous movements of the carriers as in the case where a spring tensioning force is applied to the filaments.

The braiding machine diagrammatically illustrated in FIG. 1 is actually a 16-carrier braiding machine, but is shown half-loaded, i.e., equipped with 8-carriers only divided into the two groups 10a, 10b. Each of the carriers is driven by a rotor formed with four transfer notches for receiving a carrier at one side and transferring it to another rotor at the opposite side. Such rotors are generally in the form of gears, commonly called horn gears, and are disposed within the flat horizontal housing 20.

FIG. 4 illustrates one of the horn gears, therein designated 40. It includes circumferential teeth 42 and four transfer notches or pockets, sometimes called horns 44, equally spaced around the circumference of the gear. FIG. 5 illustrates eight of such horn gears 40 arrayed in a circular array around the braiding axis BA and intermeshing with each other so that each horn gear is rotated about its respective axis 46 but in an opposite direction with respect to the adjacent gears on its opposite sides. Thus, with respect to the eight horn gears 40 shown in FIG. 5, one group 40a of alternate horn gears rotate clockwise about their respective axes 46a, as shown by arrow 48a, whereas the other group 40b of horn gears rotate in the opposite direction, e.g., counter-clockwise, about their respective axes 46b.

As well known in braiding machines of this type, the rotation of each horn gear 40 about its respective axis 46 causes a carrier 10 to be received in a notch 44 from the horn gear at one side and to be transferred to the horn gear at the opposite side. The arrangement is such that the rotation of the two groups of horn gears 40a, 40b in opposite directions around their respective axes 46a, 46b is effective to drive the two groups of carriers 10a, 10b in opposite directions around the braiding axis BA, and along circuitous paths extending radially inwardly and outwardly with respect to the braiding axis. The results is to interweave the filaments 14 of the spools 12 carried by the two groups of carriers 10a, 10b as the filaments converge at the braiding guide 16 to form the braid 70 around the mandrel 60.

The mechanism for rotating the horn gears 40a, 40b, such as to drive the carriers 10a, 10b in opposite directions along their respective serpentine paths, is well known in braiding machines of this type, as described for example in the published literature available with respect to the two commercial designs of braiding machines referred to above and incorporated herein by reference.

Such braiding machines are capable of producing various types of braid patterns, according to the manner of loading the horn gears 40. For purposes of example, three such braiding patterns are described below with respect to FIGS. 4–6, FIGS. 7–9, and FIGS. 10–12, respectively.

FIGS. 4–6 relate to producing a regular braid pattern, which is the most commonly used one, sometimes called a Herringbone Pattern. In such a pattern, each filament of carriers group 10a is passed over and under two filaments of carrier group 10b. To produce this pattern, each horn gear 40 is loaded with a carrier 10 as shown in FIG. 4, namely with alternative notches 44 occupied by a carrier, whereas the remaining alternate notches 44 are not occupied by a carrier.

FIG. 5 illustrates the manner in which the carriers 10 are transferred from one horn gear 40 to the next as each horn gear rotates about its respective axis 46. As shown by arrow 48a in FIG. 5, it will be assumed that the horn gears of group 40a are rotated clockwise about their respective axis 46a, whereas the horn gears of group 40b are rotated counter-clockwise about their respective axes 46b as indicated by arrow 48b.

FIG. 6 illustrates the braid pattern 51 produced in this set-up, wherein it will be seen that each filament 14a from the carriers 10a rotating in one direction about the braiding axis BA is interweaved over two and under two filaments 14b of the carriers 10b rotating in the opposite direction around the braiding axis.

Figure 7:
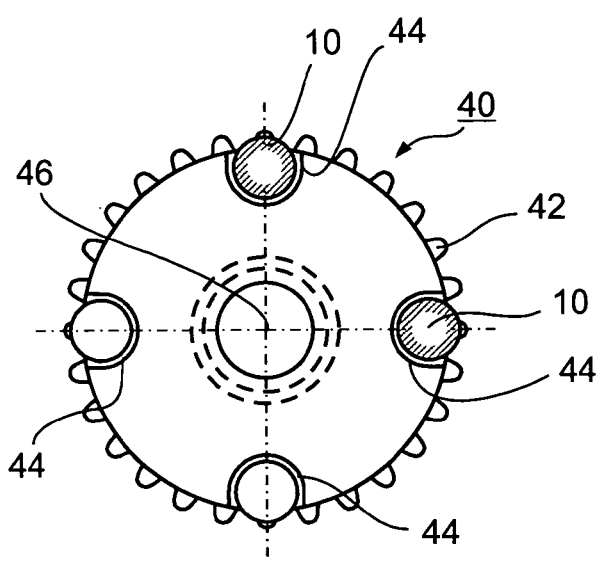
FIGS. 7 and 8 illustrate another loading arrangement for producing another broad pattern, commonly called a Diamond Pattern, in which two filaments of one group of spools are interleaved under and over two filaments of the other group of spools.
Figure 8:
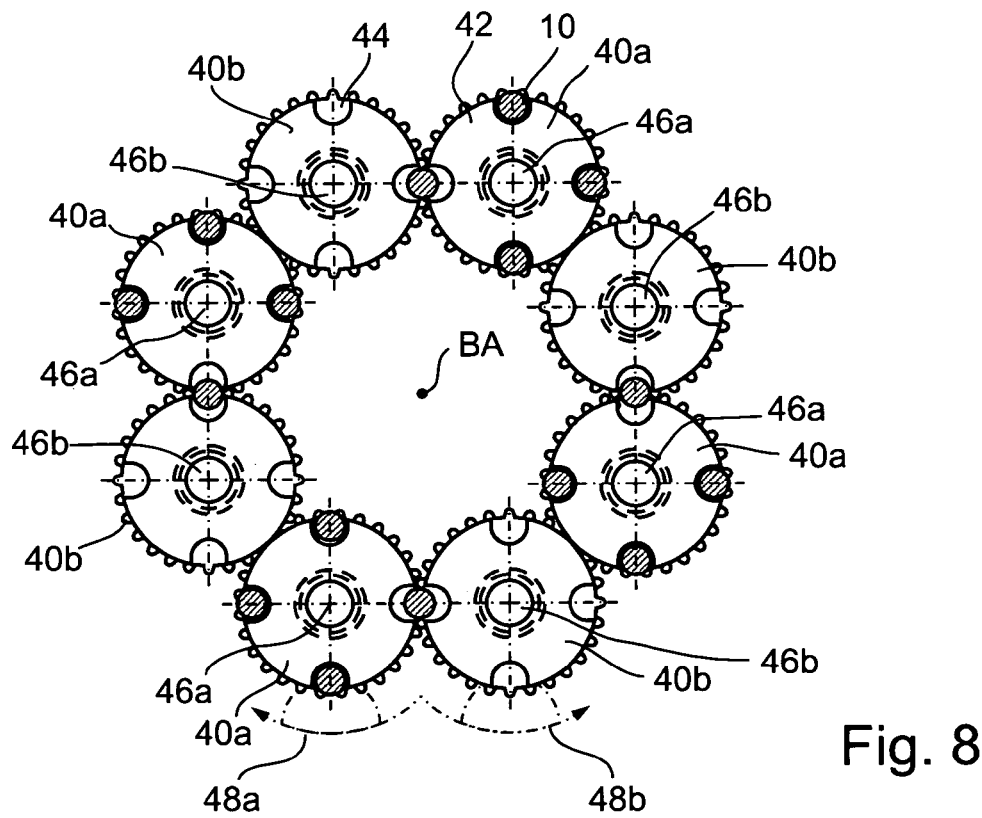

FIG. 7 illustrates the set-up of the horn gears 40 for producing a diamond braid pattern, in which two filaments 14a from carriers 10a rotating in one direction are interweaved over and under two filaments 14b from carriers 10b rotating in the opposite direction. FIG. 7 illustrates the loading arrangement for the horn gears to produce such a pattern, in which it will be seen that two adjacent notches 44 are loaded with a carrier, whereas the remaining two adjacent notches are not loaded. FIG. 8 illustrates how the carriers are transferred from one horn gear to the next during the rotation of all the horn gears about their respective axes 46. Thus, the clockwise rotation of horn gears 40a, about their respective axes 46a, as shown by arrow 48a, effects the clockwise transfer of the carriers 10a around the braiding axis BA; whereas the counter-clockwise rotation of the horn gears 40b about their respective axes 46b, as shown by arrow 48b, effects the counter-clockwise transfer of the carriers 10b around the braiding axis BA.

Figure 9:
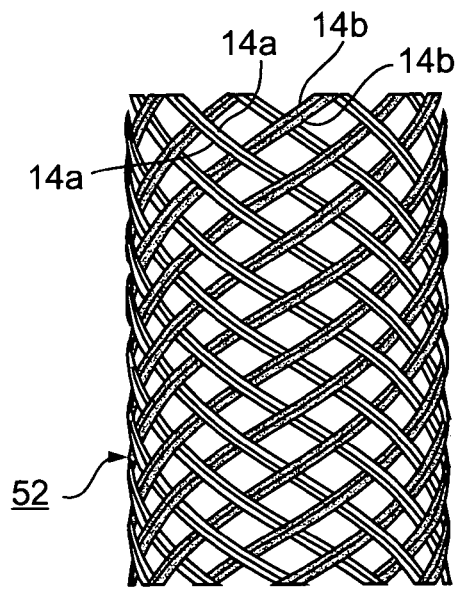
FIG. 9 illustrates the Diamond Pattern produced by the loading arrangement of FIGS. 7 and 8.

FIG. 9 illustrates the braid pattern 52 so produced, wherein it will be seen that two filaments 14a from carriers 10a rotated in the clockwise direction are contiguous and interwoven over and under two contiguous filaments 14b of the carriers 10b rotated by the horn gears 40b in the counter-clockwise direction.

Figure 10:
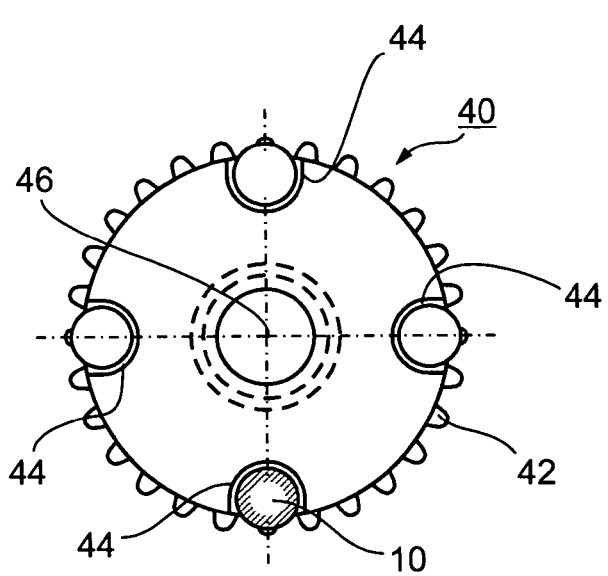
FIGS. 10 and 11 illustrate a further loading arrangement for producing another Diamond Pattern in which each filament of one group of spools is interweaved under and over a single filament of the second group of spools.
Figure 12:
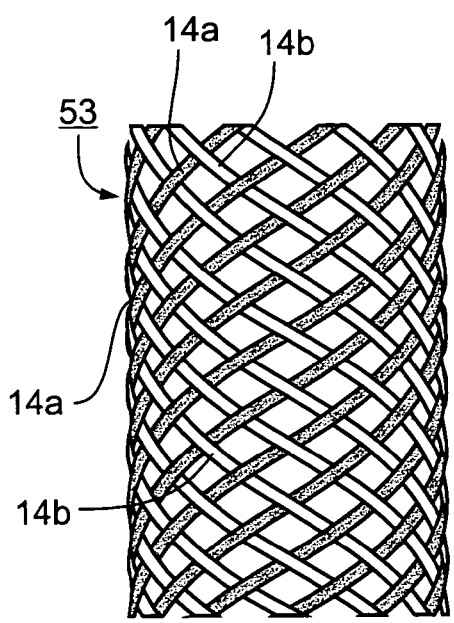
FIG. 12 illustrates the Diamond Pattern produced by the loading arrangement of FIGS. 10 and 11.
Figure 11:
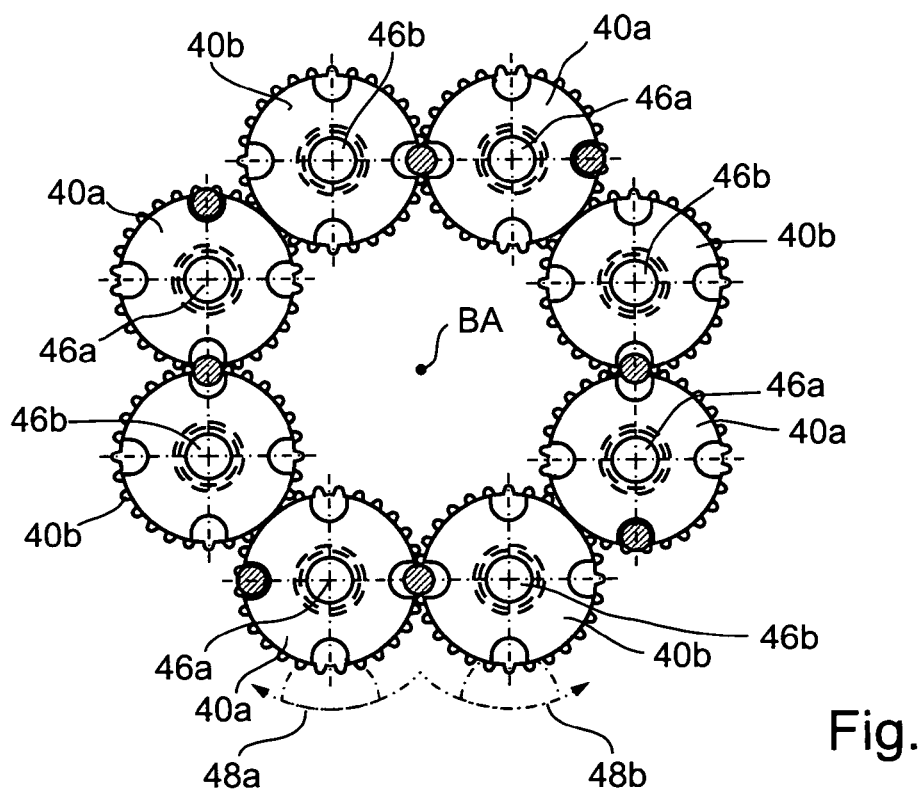

FIG. 10–12 illustrate the manner of producing a braid pattern also of a diamond configuration but in which each filament 14a from the carriers 10a is interwoven over and under a single filament 14b from the carriers 10b. As shown in FIG. 10, to produce such a pattern, the horn gears 40 are loaded with a carrier 10 in only one of the notches 44, the remaining three notches 44 being without carriers. Thus, as shown in FIG. 11, the horn gears 40a rotating in the clockwise direction about their respective axes 46a, as indicated by arrow 48a, effect the transfer of the carriers 10a in the clockwise direction about the braiding axis BA, whereas the horn gears 40b rotating in the counter-clockwise direction about their respective axes 46b, as indicated by arrow 48b in FIG. 11, effect the transfer of the carriers 10b in the counter-clockwise direction about the braiding axis.

FIG. 12 illustrates the braid pattern 53 so produced, wherein it will be seen that each filament 14a of a carrier 10a is interwoven over and under each filament 14b of a carrier 10b.

Further details of the construction of such braiding machines, and the manner of their use in producing various braid patterns, are available in the published literature of the above-cited suppliers of such machines incorporated herein by reference as background material.

The invention of the present application is concerned primarily with the manner of producing flared ends in the braided tubes, and also the construction of the mandrel 60 of FIG. 1 for this purpose.

Manner of Producing Flared Ends in Braided Tubes (FIG. 13–18b)

Figure 13:
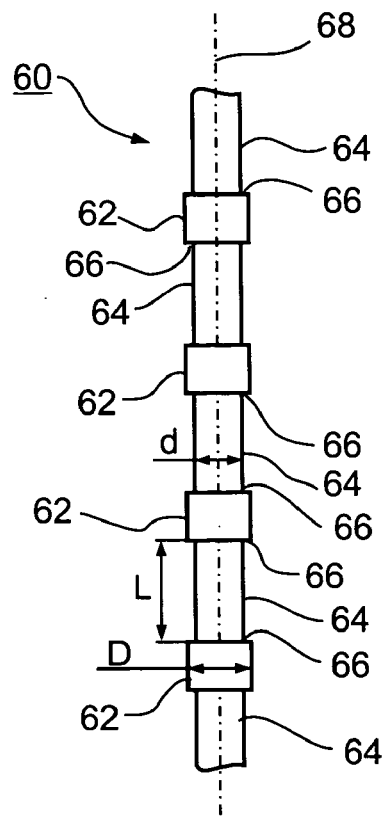
FIG. 13 illustrates the general construction of a mandrel for use in the braiding machine of FIG. 1 to produce tubular braids having flared ends.
Figure 15:
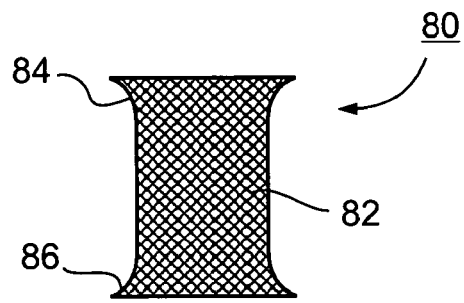
FIG. 15 illustrates the braided tube implant device after having been cut from the braided tubing in either of the manners illustrated in FIG. 14a or 14b.

The mandrel 60 illustrated in FIG. 1, and more particularly illustrated in FIG. 13, is especially constructed so as to enable the braiding machine as described above with respect to FIGS. 1–12 to be used for producing tubular braid segments 80 having two opposing outwardly flared ends as shown in FIG. 15, making them especially useful as medical intraluminal implants.

Thus, as shown in FIG. 13, the mandrel 60 around which the tubular braiding is applied by the braiding machine, is of a length many times that of the tubular braid to be produced thereon, therein generally designated 80 in FIG. 15. As shown in FIG. 13, the mandrel 60 is of cylindrical, conical, or tapered configuration and includes a plurality of large-diameter annular sections 62 at spaced locations along the length of the mandrel alternating with small-diameter sections 64 between each pair of large-diameter sections 62. As further shown in FIG. 13, each small-diameter section 64 of the mandrel is joined to a large-diameter section 62 by a juncture wall 66. In a first preferred embodiment juncture wall 66 extends substantially perpendicularly to the longitudinal axis 68 of the mandrel 60. In a second preferred embodiment juncture wall 66 is defined by a taper or chamfer between large diameter 62 and small diameter 64, the chamfer being formed by a conical portion of either small diameter section 64 or large diameter section 62.

While FIG. 13 illustrates both the large-diameter section 62 and the small-diameter section 64 as cylindrical in shape, it will be appreciated that either one, or both, may be of conical, oval, or other shape, and that the large-diameter section 62 may be merely a conical flaring at one or both ends of the cylindrical, conical or tapered section 64.

Figure 14A:
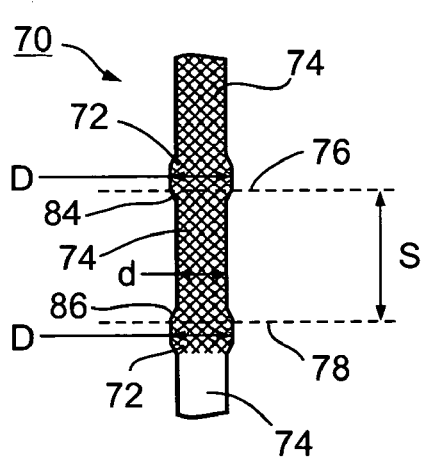
FIGS. 14a and 14b diagrammatically illustrate two manners of cutting the braided tubing applied to the mandrel by the braiding machine in order to cause opposite ends of the braided tube implant device to be outwardly flared, making it particularly useful as an intraluminal implant.

FIG. 14a illustrates the tubular braiding 70 produced on the mandrel 60 (FIG. 13) by the apparatus described above with respect to FIGS. 1–12. Since such a tubular braiding conforms to the outer surface of the mandrel 60, the tubular braiding 70 is also in the form of a continuous tube having large-diameter sections 72 of an outer diameter "D" spaced at the opposite ends of small-diameter sections 74 of a diameter "d". It is understood that diameter "D" and "d" are not fixed and may have variable dimensions along the length of the mandrel and braiding 70, depending on the width desired and selected.

The continuous length of tubular braiding 70 illustrated in FIG. 14a is cut to produce a plurality of the tubular braid segments, shown at 80 in FIG. 15. Each of the tubular braid segments 80 cut from the continuous tubular braiding 70 includes a main section 82 having outwardly flared sections 84, 86 at its opposite ends.

In order to produce such tubular braid segments 80, the continuous tubular braid 70 is cut along lines 76 and 78, in FIG. 14a, at the large-diameter braid sections 72. FIG. 14a illustrates the distance "S" between the cut line 76 and 78 is slightly larger than the length "L" of each small-diameter section 64 of the mandrel 60 (FIG. 13). However, since the braid enlarges in diameter before the large diameter mandrel section 62, the distance "S" may actually be shorter than the mandrel length "L". Cutting the continuous tubes of braiding 70 along the cut lines 76, 78, thus produces an outwardly-flared end 84, 86 (FIG. 15) at each of the opposite ends of the main section 82 of the braided tube 80 so formed.

The cut lines 76, 78, may be along mid-lines of the large-diameter sections 72, in which case the braided tubes 80 produced from the continuous tubular braiding 70 would require little if any trimming. Preferably, however, as shown in FIG. 14a, the cut lines 76, 78, are not precisely along the mid-lines of the respective large-diameter sections 72, but are closer to the small-diameter sections 74, so that some trimming would be required in the tubular braid segments produced from the continuous tubular braiding 70. As shown in FIG. 14a, the flared ends 84, 86 are formed close to the beginning of the transition from the small-diameter sections 74 to the large diameter sections 72. In a first preferred embodiment, the mandrel is stepped at this transition as shown in FIG. 13, such that the braid does not actually contact the mandrel at the transition where the cut line is made. In a second preferred embodiment an appropriate chamfer may be at the diameter transition, and the braid may contact the mandrel along the chamfer.

Figure 14B:
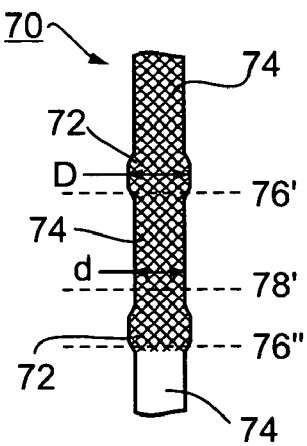

FIG. 14b illustrates another manner of cutting the continuous tubular braiding 70 in order to produce individual tubular braid segments 80 outwardly flared at both ends as shown in FIG. 15. Thus, as shown in FIG. 14b, one cut 76' may be formed in the braided transition region (or in the braided large-diameter region) of the earlier-formed braid to produce the flaring at that end. The second cut, shown at 78' in FIG. 14b, may be at the small-diameter region d in the later-formed braid. In such case, the ends of the filaments in the tubular braid segment 80 defined by the upper (earlier-formed) side of second cut line 78', will flare outwardly because of the release of the stress condition in the filaments as will be described further below.

Figure 14C:
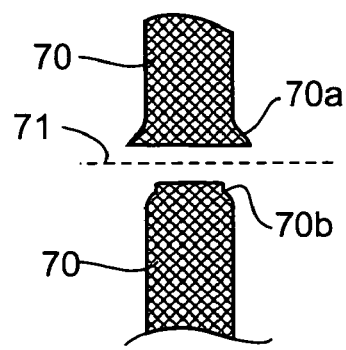
FIG. 14c is a diagram helpful in explaining how the outwardly flared end is produced in FIG. 14b with respect to the cut line at the portion of the tubular braid formed by the small-diameter section of the mandrel.

The manner in which the tubular braid segment 80 flares outwardly along the cut line 78' of FIG. 14b will be better understood by reference to the diagram of FIG. 14c.

Thus, when a continuous braided tube, shown at 70 in FIG. 14c, is progressively produced in the manner illustrated in FIG. 1, i.e., progressively from the upper end towards the lower end, the interweaving action of the filaments introduces stresses in the filaments forming the braid. If the tubular braid is cut along line 71 shown in FIG. 14c, these stresses are released to deform the ends of the two portions of the braid produced by the cut, as follows: the cut ends of the filaments in the upper portion of the braid (i.e., above the cut line 71), which had been earlier-formed during the braiding process, tend to flare outwardly, as shown at 70a; whereas the cut ends of the filaments in the lower portion of the braid, (i.e., below the cut line 71), having been produced later, tend to converge inwardly, as shown at 70b.

This tendency of flaring outwardly of the cut end of the portion of the braided tube formed earlier as shown at 70a in FIG. 14c, and the converging tendency of the cut end of the later-produced portion of the braid, as shown at 70b in FIG. 14c, occurs at both sides of the cut line 78' in FIG. 14b, since that cut line is along the portion of the braid formed by the small-diameter section 74 of the mandrel. Accordingly, when the technique of FIG. 14b is used for producing the tubular braid segment 80 shown in FIG. 15, with both ends outwardly flared, cut line 76' in FIG. 14b will produce one flared end of the respective tubular braid segment, and cut line 78' will produce the other flared end of the tubular braid segment so produced. The portion of the braid between cut line 78' and the next cut line 76" may have to be trimmed from the respective tubular braid segment.

To enable such tubular braid segments to be used as intraluminal implants, it is important that there be no convergence at either end of the tubular braid segment, since such convergence would interfere with the flow of the blood. Providing some outward flaring at both ends of the tubular braid segment thus assures that there will be no convergence at either end. The amount of outward flaring, however, can vary as desired.

FIG. 16 illustrates a mandrel, therein generally designated 90, constructed of a plurality of modular units 91 which may be conveniently removable, one after the other, to facilitate the removal of a tubular braid segment 80 of FIG. 15 after having been cut from the continuous tubular braiding 70 formed on the mandrel 90.

As shown in FIG. 16, each modular unit 91 includes a cylindrical, conical or tapered section 92 formed at either one or both ends with an enlarged head 93. Each enlarged head could be formed as a cylindrical, conical or tapered protrusion and with an axially-extending cavity or bore 94 of a diameter to receive the end of the cylindrical, conical or tapered section 92 of another like modular unit 91. Thus, mandrel 90 is constructed by assembling a plurality of the modular units 91, with the end of section 92 of each modular unit received within the cavity 94 formed in the enlarged-head of the adjacent modular unit. It will be appreciated that bore 94 could extend completely through the respective modular unit 91 to enable a plurality of such modular units to be assembled on a common shaft; also that the modular units could be provided with enlarged heads at both ends of alternatingly cylindrical, conical or tapered sections 92 connecting heads of such units.

The cylindrical, conical or tapered section 92 of each modular unit is retained within cavity 94 formed in the enlarged head of the next adjacent modular unit 91 by a press-fit, a screw or any other adapter or fastening means. This enables a plurality of such modular units to be conveniently assembled. It further enables each modular unit 91 to be removed one after the other to facilitate the removal of a tubular braid segment 80 after having been cut from the continuous tubular braiding 70.

Many other techniques could be used for making the mandrel of a modular construction. For example, all the modular units could be hollow units, or otherwise formed with through openings, for assembling them on an elongated shaft in a manner to enable them to be individually removable to facilitate removal of a tubular braid segment 80 of FIG. 15 after having been cut from the continuous tubular braiding 70. When the modular units are assembled on the shaft, they could be retained thereon, e.g., by a press-fit, by fasteners applied to the opposite ends of the shaft, by an adhesive, etc. In addition, each modular unit 91 could be constructed of two separate sections 92, 93 secured together in any suitable manner. Hollow modular units 91 or modular units with cavities could also be assembled on a non-circular shaft thus enabling efficient cleaning and flushing of gaps between assembled parts.

FIGS. 17–18*b* illustrate another construction of mandrel that may be used in order to facilitate the convenient removal of each tubular braid segment 80 after having been cut from the continuous tubular braiding 70 as described above. Such a mandrel, generally designated 95, is constructed of a cylindrical or conical rod 96 of uniform diameter having a plurality of elastic rings 97 removably received at spaced locations along the length of the rod to define the large-diameter sections, corresponding to sections 62 in FIG. 13. Each of the rings 97 is normally of a non-circular configuration, as illustrated in FIG. 18*a*, so as to be elastically retained on the cylindrical or conical rod 96 when producing the continuous tubular braiding 70 as described above with respect to FIG. 14. In a preferred embodiment, rings 97 are designed to be nearly circular when placed on rod 96. However, as each tubular braid segment 80 is cut from the continuous tubular braiding 70 along cut lines 76, 78, as shown in FIG. 14*a*, or along cut lines 76', 78', as shown in FIG. 14*b*, the respective elastic ring 97 may be manually distorted towards a circular configuration, as shown in FIG. 18*b*, by merely squeezing the ring, to permit the ring to be removed, and thereby, to permit the removal of the next tubular braid segment 80 cut from the continuous tubular braiding 70.

FIGS. 19*a*–19*k* illustrate further constructions and configurations that may be used for the mandrel. For purposes of illustration the phrase facing the braiding point is meant to indicate a taper which after being braided faces, or is tapered towards, the braiding point. The phrase facing away from the braiding point is meant to include a taper that prior to being braided faces away from the braiding point. FIGS. 19*a*–19*c* show a cross section of mandrel 95 of FIG. 17. In FIG. 19*a*, ring 97 is cylindrical and in FIG. 19*b* ring 97 is conical facing the braiding point. In FIG. 19*c* ring 97 is conical facing away from braiding point. FIGS. 19*d*, 19*e* show a cross section of further embodiments of mandrel 90 of FIG. 16 in which enlarged head 93 is cylindrical. In FIG. 19*d*, flare 84 of FIG. 15 is formed over enlarged head 93 and cylindrical, conical or tapered section 92 of the same modular unit 91. In FIG. 19*e*, flare 84 of FIG. 15 is formed over enlarged head 93 and cylindrical, conical or tapered section 92 of a connected modular unit 91. FIG. 19*f* shows a cross section of a further embodiment of mandrel 90 of FIG. 16 in which enlarged head 93 is conical facing the braiding point and flare 84 of FIG. 15 is formed over enlarged head 93 and cylindrical, conical or tapered section 92 of the same modular unit 91. FIG. 19*g* shows a cross section of a further embodiment of mandrel 90 of FIG. 16 in which enlarged head 93 and cylindrical or conical section 92 are formed from individual parts connected together. FIG. 19*h* shows a cross section of a further embodiment of mandrel 90 of FIG. 16, in which enlarged head 93 is conical facing away from the braiding point; and flare 84 of FIG. 15 is formed over enlarged head 93 and cylindrical, conical or tapered section 92 of the same modular unit 91. FIG. 19*i* shows a cross section of a further embodiment of mandrel 90 of FIG. 16, in which enlarged head 93 is cylindrical, flare 84 of FIG. 15 is formed over enlarged head 93 and conical section 92 of the same modular unit 91, and conical section 92 faces the braiding point. FIG. 19*j* shows a cross section of a further embodiment of mandrel 90 of FIG. 16 in which enlarged head 93 is cylindrical, flare 84 of FIG. 15 is formed over enlarged head 93 and conical section 92 of the connected modular unit 91 and conical section 92 faces away from the braiding point. FIG. 19*k* shows a cross section of a further embodiment of mandrel 90 of FIG. 16 in which enlarged head 93 is conical facing the braiding point, flare 84 of FIG. 15 is formed over enlarged head 93 and conical section 92 of the connected modular unit 91, and conical section 92 faces away from the braiding point.

The above illustrations are not meant to be limiting or exhaustive in any way, and other combinations of rings 97, enlarged heads 93 and cylindrical, conical or tapered sections 92 of modular unit 91 are possible without exceeding the scope of the invention.

One advantage of using a conical, tapered or other shaped mandrel, is that it enables an improved implantation of the braided device whose shape, closely follows that of the shaped mandrel. Thus, a braided intraluminal implant, formed on a shaped mandrel, may more closely match the shape of the target implantation area with appropriate oversizing. Furthermore, an appropriately shaped braided intraluminal implant, formed on a shaped mandrel, may exhibit improved appositioning and ultimate fixation to the lumen wall.

Another advantage of a conical, tapered or other shaped mandrel is the ability to change the effective braiding angle over the length of the implant, with a fixed braiding machine pitch. The tension, radial force and local stiffness of the implant may be changed over the length of the implant without changing any braiding machine parameters.

While the invention has been described with respect to several preferred embodiments, it will be appreciated that these are set forth merely for purposes of example, and that many variations may be made. For example, the invention could be implemented in weaving apparatus or braiding machine wherein the mandrel extends along a horizontal braiding axis, rather than a vertical braiding axis. Many other variations, modifications and applications of the invention will be apparent.

What is claimed is:

1. A method of making a braided intraluminal implant, comprising:

providing a mandrel having at least one small-diameter section joined at least at one end to a large-diameter section;

interweaving a plurality of filaments devoid of a binder material to form a tubular braid enclosing at least a part of said small-diameter section and at least a part of said large-diameter section;

and, while said filaments remain devoid of a binder material such that the filaments are supported solely in said tubular braid by said mandrel, cutting said tubular braid to produce a tubular braid segment having outwardly flared ends at its opposite ends.

2. The method according to claim 1, wherein said cutting of said tubular braid is accomplished at at least one point wherein said tubular braid does not enclose a part of said large diameter section, such that the release of stresses in the filaments of the tubular braid produces a said flared end.

3. The method according to claim 1, wherein said small-diameter section of the mandrel is joined at both of its opposite ends to a large-diameter section; and wherein said tubular braid is cut along a portion thereof formed by a large-diameter section of the mandrel to produce each of said outwardly flared ends of the tubular braid segment.

4. The method according to claim 1, wherein said tubular braid is cut along a first cut line on a portion thereof formed by said large-diameter section of the mandrel to produce an outward flaring at said first cut line defining one end of the tubular braid segment; said tubular braid being cut along a second cut line on a portion thereof formed by the small-diameter segment of the mandrel at a location of the tubular braid where the release of stresses in the filaments of the tubular braid inherently produces an outward flaring of the braid at said second cut line defining the opposite end of the tubular braid segment.

5. The method according to claim 1, wherein said mandrel is of a length many limes that of the tubular braid segment to be produced, and includes a plurality of small-diameter sections alternating with a plurality of large-diameter sections; and wherein said tubular braid is formed on said mandrel in a continuous length and is cut into a plurality of said tubular braid segments.

6. The method according to claim 5, wherein at least a portion of said small-diameter segments arc of cylindrical, conical or tapered configuration.

7. The method according to claim 5, wherein at least a portion of said large diameter segments are of cylindrical, conical or tapered configuration.

8. The method according to claim 5, wherein said mandrel is constructed of a plurality of modular units, each having a cylindrical, conical or tapered section formed at one end with an enlarged head; each of said enlarged heads being integrally formed with an axially-extending bore of a diameter to receive the end of the cylindrical, conical or tapered section of another modular unit.

9. The method according to claim 8, wherein, after a tubular braid segment is cut from said continuous length, a modular unit is removed to permit the cut tubular braid segment to be conveniently removed.

10. The method according to claim 5, wherein said mandrel is constructed of a cylindrical, conical or tapered rod having a plurality of rings removably received at spaced locations along the length of said rod to define said large-diameter sections of the mandrel.

11. The method according to claim 10, wherein each of said rings is an elastic ring of a non-circular configuration so as to be elastically retained on said rod and conveniently removable therefrom by manually distorting the ring towards a circular configuration.

12. The method according to claim 10, wherein, after a tubular braid segment is cut from said continuous length a ring is removed from said rod to permit the cut tubular braid segment to be conveniently removed.

13. A mandrel for use with a braiding machine for making braided intraluminal implants; said mandrel comprising at least one small-diameter section joined at least at one end to a large-diameter-section;

said mandrel being dimensioned to enable a plurality of filaments to be interwoven thereon to produce braided intraluminal implants of a diameter corresponding to said small-diameter section and having at least one flared end formed by said large-diameter section;

said mandrel being of a length many times that of the braided intraluminal implants to be made, such that a continuous length of a tubular braid may be formed on said mandrel and then cut into a plurality of said tubular braid segments;

said mandrel being constructed of a plurality of modular units, each having a cylindrical, conical or tapered section integrally formed at one end with an enlarged head, having an axially-extending bore of a diameter to receive the end of the cylindrical, conical or tapered section of another modular unit.

14. A mandrel for use with a braiding machine for making braided intraluminal implants:

said mandrel comprising at least one small-diameter section joined at least at one end to a lame-diameter-section;

said mandrel being dimensioned to enable a plurality of filaments to be interwoven thereon to produce braided intraluminal implants of a diameter corresponding to said small-diameter section and having at least one flared end formed by said large-diameter section;

wherein said mandrel is constructed of a cylindrical, conical or tapered rod having a plurality of rings removably received at spaced locations along the length of said rod to define said large-diameter sections of the mandrel;

and wherein each of said rings is an elastic ring of a non-circular configuration so as to be elastically retained on said rod and conveniently removable therefrom by manually distorting the ring towards a circular configuration.

15. Apparatus for making braided intraluminal implants, comprising:

a mandrel according to claim 14;

and a braiding machine for interweaving a plurality of filaments around said mandrel.

* * * * *